US012733913B2

(12) United States Patent
Fan et al.

(10) Patent No.: US 12,733,913 B2
(45) Date of Patent: Sep. 15, 2026

(54) ULTRASOUND ATTENUATION COEFFICIENT ESTIMATION USING ABERRATION COMPENSATION AND REFERENCE PHANTOMS

(71) Applicant: Shantou Institute of Ultrasonic Instruments Co., Ltd., Shantou (CN)

(72) Inventors: Liexiang Fan, Shantou (CN); Bin Huang, Shantou (CN); Bin Li, Shantou (CN); Yu Wang, Shantou (CN); Haomiao Qiu, Shantou (CN); Yuqiang Kang, Shantou (CN)

(73) Assignee: Shantou Institute of Ultrasonic Instruments Co., Ltd., Shantou (CN)

( * ) Notice: Subject to any disclaimer, the term of this patent is extended or adjusted under 35 U.S.C. 154(b) by 128 days.

(21) Appl. No.: 19/000,571

(22) Filed: Dec. 23, 2024

(65) Prior Publication Data

US 2025/0241626 A1 Jul. 31, 2025

Related U.S. Application Data

(63) Continuation of application No. PCT/CN2024/074594, filed on Jan. 30, 2024.

(30) Foreign Application Priority Data

Jan. 29, 2024 (CN) ......................... 202410115721.0

(51) Int. Cl.
*A61B 8/00* (2006.01)
*G01S 7/52* (2006.01)

(52) U.S. Cl.
CPC .......... *A61B 8/587* (2013.01); *G01S 7/52004* (2013.01)

(58) Field of Classification Search
CPC ....... A61B 8/587; A61B 8/085; A61B 8/0858; A61B 8/5215; G01S 7/52004; G06F 18/10; G06F 2218/04
See application file for complete search history.

(56) References Cited

U.S. PATENT DOCUMENTS

| | | | | |
|---|---|---|---|---|
| 11,464,463 | B2 * | 10/2022 | Sun | A61B 6/032 |
| 11,986,269 | B2 * | 5/2024 | Wang | G01N 29/42 |
| 2004/0054281 | A1 * | 3/2004 | Adam | A61B 8/587 600/437 |

(Continued)

*Primary Examiner* — Sanjay Cattungal
(74) *Attorney, Agent, or Firm* — Westbridge IP LLC

(57) ABSTRACT

Disclosed is a method for estimating ultrasound attenuation coefficient by use of aberration compensation and the reference phantom method. Measurements on a human sample at a single transmit frequency and on multiple reference phantoms at a plurality of transmit frequencies are performed respectively. The center frequencies of the echo signals at the depth of the top edge of the region of interest are calculated. A specific reference phantom at a specific transmit frequency is selected by the echo signals whose center frequencies are closest to the center frequencies of the echo signals from the human sample at the aforementioned depth to compensate for the aberration. Then the spectra of the echo signals from the selected reference phantom at the selected transmit frequency and the spectra from the echo signals from the human sample are used to estimate the attenuation coefficient of the human sample by following the reference phantom method.

2 Claims, 1 Drawing Sheet

Reference phantom

Human sample to be measured d

Transition zone (Skin, bones, blood vessel etc.)

Region of Interest

Depth d is the depth at the top edge of the region of interest to be measured

Region of Interest

(56) References Cited

U.S. PATENT DOCUMENTS

2013/0199299 A1* 8/2013 Wang .................. A61B 5/0095 73/655
2013/0289381 A1* 10/2013 Oraevsky ........... A61B 5/14552 600/407
2013/0301380 A1* 11/2013 Oraevsky ............. A61B 5/0035 367/7
2013/0338498 A1* 12/2013 Emelianov ........... A61B 5/0035 600/431
2020/0225347 A1* 7/2020 Parker ................. G01S 15/8977
2021/0018620 A1* 1/2021 Oraevsky ............. A61B 5/0033
2022/0054001 A1* 2/2022 Zhu .......................... A61B 1/07
2022/0212036 A1* 7/2022 Naqa ........................ A61B 8/08
2024/0237965 A1* 7/2024 Xu ....................... A61B 8/0858
2025/0116852 A1* 4/2025 Cheng .................. G01N 21/636
2025/0241626 A1* 7/2025 Fan ........................ A61B 8/587
2026/0102143 A1* 4/2026 Besson .................. A61B 8/485

* cited by examiner

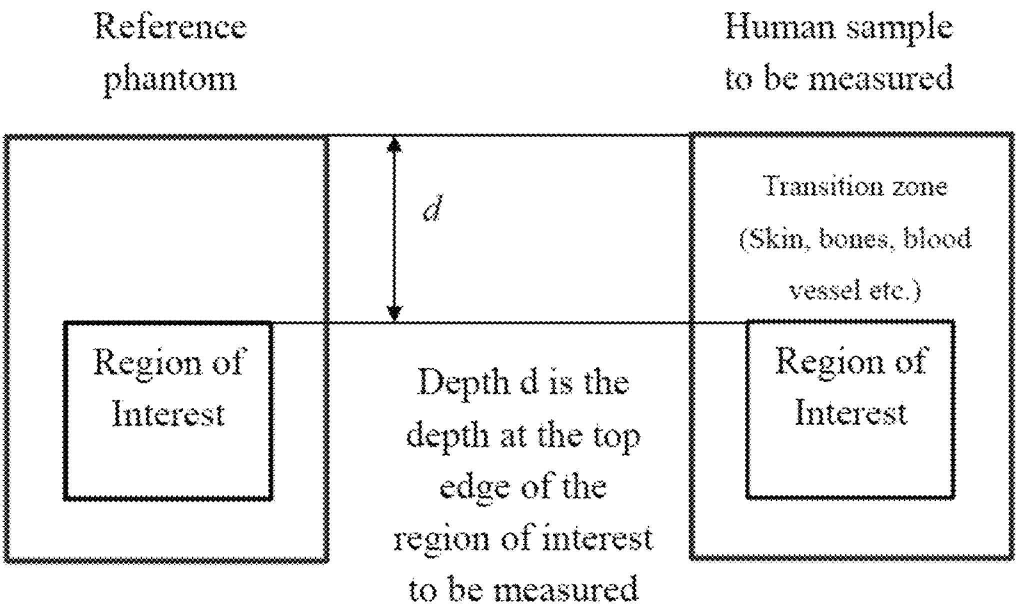
Reference phantom
Human sample to be measured
d
Transition zone (Skin, bones, blood vessel etc.)
Region of Interest
Region of Interest
Depth d is the depth at the top edge of the region of interest to be measured

ULTRASOUND ATTENUATION COEFFICIENT ESTIMATION USING ABERRATION COMPENSATION AND REFERENCE PHANTOMS

CROSS-REFERENCE TO RELATED APPLICATIONS

The present application is a continuation application of International Application No. PCT/CN2024/074594, filed on Jan. 30, 2024, which claims priority to Chinese Patent No. 202410115721.0, filed on Jan. 29, 2024. All of the aforementioned applications are incorporated herein by reference in their entireties.

TECHNICAL FIELD

The application relates to the technical field of quantitative ultrasound, in particular to a method for estimating ultrasound attenuation coefficient using aberration compensation and reference phantom method.

BACKGROUND

In clinical diagnosis of fatty liver, ultrasound attenuation coefficients of liver tissue are generally estimated to determine whether liver tissue lesions occur and what is the extent of lesions. The current method of estimating ultrasound attenuation coefficient is to use a calibrated reference phantom, specifically to measure the power spectra of the echo signals from a human sample and a reference phantom with calibrated attenuation coefficient respectively under the same transmitting and receiving conditions, thereby the ratio of power spectra of the human sample and the reference phantom is a function of depth and the differences of the attenuation coefficients between human sample and the reference phantom. The attenuation coefficient of the human sample is specifically calculated through the following formula:

$$\alpha_s(f) = -\frac{d\left(\ln\left(\frac{S_s(f, z)}{S_P(f, z)}\right)\right)}{4dz} + \alpha_P(f),$$

wherein $\alpha_s$(f) is the attenuation coefficient of the sample, $S_s$(f, z) is the power spectra of the echo signals from the human sample measured at a certain transmit frequency, and $S_P$(f, z) is the power spectra of the echo signals from the reference phantom measured at a certain transmit frequency. When the transmit frequency is fixed, the ratio of $S_s$(f, z) and $S_P$ (f, z) is a function of the measured depth z; and $$\frac{d\left(\ln\left(\frac{S_s(f, z)}{S_i(f, z)}\right)\right)}{4dz}$$

is the slope or differential value of the logarithm of the power spectra ratio versus the depth in the measured area. When estimating ultrasound attenuation coefficient by the reference phantom method aforementioned, it is assumed that the acoustic paths of the reference phantom and the human body are the same, whereas in human body, ultrasound wave passes through transition zones with different sound velocities and attenuation coefficients such as skin, bones, blood vessels and fat before reaching the target region. This is different from the assumption that the whole velocities and attenuation coefficients are uniform as in the reference phantom. Due to the deviations and differences in the respective acoustic paths between the human body and the reference phantom, the ultrasound attenuation coefficient of the human sample estimated by the conventional reference phantom method has large variation and biases.

SUMMARY

The application aims to provide a method for estimating ultrasound attenuation coefficient by using aberration compensation and reference phantoms, wherein the method can effectively compensate deviations caused by different acoustic paths between the human body and the reference phantoms, thus improve the accuracy of ultrasound attenuation coefficient estimation.

In order to achieve the aforementioned goal, the present application utilizes the following technical solution to estimate ultrasound attenuation coefficient using aberration compensation and reference phantoms: the human sample and N reference phantoms with different attenuation coefficients $\alpha_1$, $\alpha_2$, $\alpha_3$, . . . $\alpha_N$ are measured and the center frequencies of the echo signals at the depth d of the human sample and the reference phantoms are calculated respectively, wherein d is the depth at the top edge of the measured region in the human body. For measurements performed on the human body and calculation of the center frequencies of the echo signals at the depth d, the echo signals are acquired and center frequencies are calculated after the transmission of a single frequency $f_0$; whereas for measurements on the N reference phantoms and calculation of the center frequencies of the echo signals at the depth d, the echo signals are acquired and center frequencies are calculated after the transmission of a plurality of m frequencies $f_1$, $f_2$, $f_3$ . . . $f_m$. From the calculated center frequencies at the depth d of the N×m acquired echo signals, a specific reference phantom $\alpha_i$ at a transmit frequency $f_j$ is selected for echo signals whose center frequencies are closest to the center frequencies of the echo signals from the human sample at the depth d. Finally, the attenuation coefficient of the human sample to be estimated is calculated according to the formula $$\alpha_s(f) = -\frac{d\left(\ln\left(\frac{S_s(f, z)}{S_i(f, z)}\right)\right)}{4dz} + \alpha_i(f),$$

wherein $\alpha_s$(f) is the attenuation coefficient of the human sample, $S_s$(f, z) is the power spectra of the echo signals of the human sample at the transmit frequency $f_0$, $S_i$(f, z) is the power spectra of the echo signals of the reference phantom at the selected transmit frequency $f_j$, $$\frac{d\left(\ln\left(\frac{S_s(f, z)}{S_i(f, z)}\right)\right)}{4dz}$$

is the slope or differential value of the logarithm of the power spectra ratio versus the depth in the measured area, and $\alpha_i$(f) is the attenuation coefficient of the selected reference phantom.

Specifically, when performing measurements on the human sample and N reference phantoms with different attenuation coefficients $\alpha_1$, $\alpha_2$, $\alpha_3$, . . . $\alpha_N$, and calculating the center frequencies of the echo signals at the depth d of the human sample and the reference phantoms respectively, the echo signals of the reference phantoms with N attenuation coefficients at m different transmit frequencies can be acquired and saved on a hard disk beforehand; The center frequencies of the echo signals at the depth d from each reference phantom at m different transmit frequencies can be calculated from the already saved data whenever needed to reduce the data acquisition time during actual measurements on the human body.

Specifically, when calculating the center frequencies of the echo signals of the human sample and the reference phantoms respectively at the depth d, the centroid method is employed by using the following formula specifically $$f_c = \frac{\int_0^\infty f|X(f)|df}{\int_0^\infty |X(f)|df},$$

where $f_c$ is the center frequency, f is the frequency of the echo signals, and X(f) is the spectra of the echo signals at the depth d.

Specifically, when calculating the attenuation coefficient of the human sample, noise reduction on the power spectra $S_s(f, z)$ of the echo signals of the human sample at the transmit frequency $f_0$, and on the power spectra $S_i(f, z)$ of the echo signals measured from the reference phantom at the transmit frequency $f_j$ is performed, and then the aforementioned formula is used to calculate the attenuation coefficient.

The beneficial effects of this method are: measurements on a human sample with a single transmit frequency and on the reference phantoms with a plurality of transmit frequencies are performed respectively, the center frequencies of the echo signals at the depth at the top edge of the region of interest is calculated, and a specific reference phantom at a specific transmit frequency is selected for the echo signals whose center frequencies are closest to the center frequencies of the echo signals from the human sample and the corresponding transmit frequency, and finally, the spectra of the echo signals from the selected reference phantom together with its corresponding transmit frequency and the spectra of the echo signals from the human sample are used to estimate the attenuation coefficient of the human sample by following the reference phantom method, thereby aberration compensation of signals caused by different acoustic paths between the human sample and reference phantoms is achieved. Consequently, this method effectively improves the accuracy of estimating ultrasound attenuation coefficient of the human sample.

BRIEF DESCRIPTION OF THE DRAWINGS

FIG. 1 illustrates a schematic diagram of the acoustic paths of a reference phantom and a human sample in an embodiment and during measurement.

DETAILED DESCRIPTION OF THE EMBODIMENTS

Embodiment 1, referring to FIG. 1, is a method for estimating ultrasound attenuation coefficient using aberration compensation and the reference phantom method comprising the following steps: measurements on a human sample and on a reference phantom with N attenuation coefficients $\alpha_1, \alpha_2, \alpha_3, \ldots \alpha_N$ are performed and the central frequencies of the echo signals of the human sample and the reference phantoms at the depth d are calculated respectively, wherein d is the depth at the top edge of the region of interest of the human sample.

When performing measurement on a human sample and calculating the center frequencies of the echo signals at the depth d, the echo signals are acquired and calculated after the transmission of a single frequency $f_0$; When performing measurements on the N reference phantoms and calculating the center frequencies of the echo signals at the depth d, the echo signals are acquired and calculated after the transmission of a plurality of m frequencies $f_1, f_2, f_3 \ldots f_m$; a specific reference phantom $\alpha_i$ at a transmit frequency $f_j$ is selected for the echo signals whose center frequencies are closest to the center frequencies of the echo signals of the human sample at the depth d from the multiple N×m echoes at the depth d obtained from the N reference phantoms at a plurality of m transmit frequencies.

Finally, the attenuation coefficient of the human sample is calculated according to the formula $$\alpha_s(f) = -\frac{d\left(\ln\left(\frac{S_s(f, z)}{S_i(f, z)}\right)\right)}{4dz} + \alpha_i(f),$$

wherein $\alpha_s(f)$ is the attenuation coefficient of the human sample, $S_s(f, z)$ is the power spectra of the echo signals of the human sample at the transmit frequency $f_0$, $S_i(f, z)$ is the power spectra of the echo signals of the reference phantom at the selected transmit frequency $f_j$, $$\frac{d\left(\ln\left(\frac{S_s(f, z)}{S_i(f, z)}\right)\right)}{4dz}$$

is the slope or differential value of the logarithm of the power spectra ratio versus the depth in the measured area, and $\alpha_i(f)$ is the attenuation coefficient of the selected reference phantom.

It should be noted that the power spectra $S_s(f, z)$ and $S_i(f, z)$ are functions of transmit frequency f and the detection depth z. When the transmit frequency is fixed, the power spectrum is a function of the detection depth z. In this embodiment, by selecting a reference phantom with a transmit frequency from the echo signals whose center frequencies are closest to the center frequencies of the echo signals from the human sample at the depth d, aberration of the echo signals caused by different acoustic paths between the human sample and reference phantoms is compensated. This effectively improves the accuracy of estimating ultrasound attenuation coefficient of the human sample.

In the estimation method of this embodiment, by using a plurality of m transmit frequencies to measure and calculate the center frequencies of the echo signals of the N reference phantoms with different attenuation coefficients, a reference phantom with a specific transmit frequency that will produce signals whose center frequencies are closest to the center frequencies of the echo signals of the human sample at the depth d can be accurately selected, thereby the efficiency of estimating ultrasound attenuation coefficient of the human sample is increased.

Specifically, when performing measurements on the human sample and the N reference phantoms with different attenuation coefficients $\alpha_1, \alpha_2, \alpha_3, \ldots \alpha_N$, and calculating the center frequencies of echo signals at the depth d of the human sample and the reference phantoms respectively, the reference phantoms with N attenuation coefficients at m different transmit frequencies are used, and echo signals for each reference phantom at m different transmit frequencies can be saved in a hard disk beforehand. During actual measurement on the human body and calculation of the center frequencies of the echo signals at the depth d, the center frequencies of echo signals at the depth d of each reference phantom at m different transmit frequencies can be calculated from the already saved echo signals whenever needed. By performing measurements on the N reference phantoms at a plurality of m transmit frequencies and saving echo data in a hard disk beforehand, the stored echo data can be retrieved at any time needed, thereby data acquisition time is reduced, and detection efficiency is improved.

Specifically, when calculating the aforementioned center frequencies of the echo signals of the human sample and the reference phantoms at the depth d, the centroid method is used for calculation by using the following formula specifically $$f_c = \frac{\int_0^\infty f|X(f)|df}{\int_0^\infty |X(f)|df},$$

where $f_c$ is the center frequency, f is the frequency of the echo signals, and X(f) is the spectra of the echo signals at the depth d. In addition to the centroid method, any method conventionally used in medical ultrasound can also be used for calculating the center frequencies of the echo signals.

Specifically in this embodiment, noise reduction is performed on the power spectra $S_s(f, z)$ of the echo signals of the human sample at the transmit frequency $f_0$, and on the power spectra $S_i(f, z)$ of the echo signals measured from the reference phantom at the transmit frequency $f_j$, and then the aforementioned formula to calculate the attenuation coefficient is used. By performing noise reduction on the power spectra of the echo signals, the accuracy of estimating ultrasound attenuation coefficient of the human sample can be further improved; specifically, noise reduction on the power spectra can be performed by filtering, or other noise reduction methods conventionally used.

Certainly, the embodiments above are preferred for the present application only, but the scope of the use of the present application is not intended to be restricted. Therefore, any equivalent changes based on the principles of the present application should be included in the protection scope of the present application.

What is claimed is:

1. A method for estimating ultrasound attenuation coefficient using aberration compensation and reference phantom method, comprising the following steps:

(a) acquiring ultrasound data on a human sample and calculating the central frequencies of echo signals at the depth d after the transmission of a single frequency $f_0$, wherein d is the depth at the top edge of the region of interest;

(b) acquiring ultrasound data on N reference phantoms with N attenuation coefficients $\alpha_1, \alpha_2, \alpha_3, \ldots \alpha_N$ after the transmission of a plurality of m frequencies $f_1, f_2, f_3 \ldots f_m$ on each phantom, and with almost the same settings as in the human study except for the transmit frequencies, and calculating the center frequencies of the echo signals at the depth d;

(c) selecting a specific reference phantom $\alpha_i$ with a specific transmit frequency $f_j$ so that the center frequencies of its echo signals are closest to the center frequencies of the echo signals from the human sample at the depth d among the central frequencies of the echo signals at the depth d calculated from the N reference phantoms at a plurality of different transmit frequencies;

(d) calculating the attenuation coefficient of the human sample according to the reference phantom method, according to the formula $$\alpha_s(f) = -\frac{d\left(\ln\left(\frac{S_s(f, z)}{S_i(f, z)}\right)\right)}{4dz} + \alpha_i(f),$$

wherein $\alpha_s(f)$ is the attenuation coefficient of the human sample to be estimated, $S_s(f, z)$ is the power spectra of the echo signals of the human sample at the transmit frequency $f_0$, $S_i(f, z)$ is the power spectra of the echo signals of the reference phantom at the selected transmit frequency $f_j$, $$\frac{d\left(\ln\left(\frac{S_s(f, z)}{S_i(f, z)}\right)\right)}{4dz}$$

is the slope or differential value of the logarithm of the power spectra ratio versus the depth in the region of interest, and $\alpha_i(f)$ is the attenuation coefficient of the selected reference phantom;

wherein, when calculating the center frequencies of the echo signals of the human sample and of the reference phantoms at the depth d, using the centroid method by the following formula specifically $$f_c = \frac{\int_0^\infty f|X(f)|df}{\int_0^\infty |X(f)|df},$$

where $f_c$ is the center frequency to be estimated, f is the frequency of the echo signals, and X(f) is the spectra of the echo signals at the depth d;

wherein before calculation of the central frequencies and the power spectra of the acquired ultrasound data, performing noise reduction on the power spectra of the echo signals of the human sample and on the power spectra of the echo signals from each reference phantom.

2. The method for estimating ultrasound attenuation coefficient using aberration compensation and the reference phantom method according to claim 1, wherein when acquiring ultrasound data on a human sample and N reference phantoms with N attenuation coefficients $\alpha_1, \alpha_2, \alpha_3, \ldots \alpha_N$ and calculating the center frequencies of the echo signals of the human sample and the N reference phantoms at the depth d, acquiring the echo signals for each reference phantom at each transmit frequencies and saving ultrasound data on a hard disk before any measurement on the human sample; and calculating the center frequencies and power spectra of the echo signals at the depth d of each reference phantom at each transmit frequency from the already saved echo signals whenever needed.

* * * * *